United States Patent
Zimmermann et al.

(10) Patent No.: US 7,119,898 B2
(45) Date of Patent: Oct. 10, 2006

(54) METHOD FOR THE DETECTION OF FLUORESCENT LIGHT

(75) Inventors: Bernhard Zimmermann, Jena (DE); Eva Simbuerger, Potsdam (DE); Mary Dickinson, Pasadena, CA (US)

(73) Assignee: Carl Zeiss Jena GmbH, Jena (DE)

( * ) Notice: Subject to any disclaimer, the term of this patent is extended or adjusted under 35 U.S.C. 154(b) by 436 days.

(21) Appl. No.: 10/763,649

(22) Filed: Jan. 23, 2004

(65) Prior Publication Data

US 2004/0246478 A1 Dec. 9, 2004

(30) Foreign Application Priority Data

Jan. 27, 2003 (DE) .................. 103 03 404

(51) Int. Cl.
*G01J 3/30* (2006.01)
(52) U.S. Cl. .................................... 356/318
(58) Field of Classification Search ......... 356/317–318
See application file for complete search history.

(56) References Cited

U.S. PATENT DOCUMENTS

| | | | | |
|---|---|---|---|---|
| 6,134,002 A | * | 10/2000 | Stimson et al. | 356/326 |
| 6,403,332 B1 | | 6/2002 | Bearman et al. | |
| 2002/0057430 A1 | * | 5/2002 | Engelhardt | 356/318 |
| 2003/0142292 A1 | * | 7/2003 | Wolleschensky et al. | 356/317 |

FOREIGN PATENT DOCUMENTS

DE 199 15 137 10/2000

OTHER PUBLICATIONS

Two-photon-3-D Mapping of Tissue Endogenous Fluorescence Species Based on Fluorescence Excitation Spectra, Lily Hsu, et al. Multiphoton Microscopy in the Biomedical Sciences, Ammasi Periasamy, Peter .C. So, Editors, vol. 4262 2001.
Sensitive Imaging of Spectrally Overlapping Fluorochromes using the LSM 510 META, Mary E. Dickinson, et al. Multiphoton Microscopy in the Biomedical Sciences II, Ammasi Periasamy, Peter .C. So, Editors, vol. 4262 2002.

* cited by examiner

*Primary Examiner*—Gregory J. Toatley, Jr.
*Assistant Examiner*—Kara Geisel
(74) *Attorney, Agent, or Firm*—Reed Smith LLP

(57) ABSTRACT

A method for the detection and evaluation of the light generated in a fluorescing specimen by a short pulse laser, wherein at least a first and a second fluorophore and/or a self-fluorescing specimen are separately irradiated with different wavelengths and the specimen light is recorded in a wavelength-dependent manner with at least one nondescanned detector as reference spectrum and a separation into individual spectra is carried out during the irradiation of at least two fluorophores and/or self-fluorescing specimens simultaneously from the measured spectrum and the reference spectra through regression analysis, wherein the wavelength of the short pulse laser is advantageously changed continuously in at least one wavelength region.

3 Claims, 1 Drawing Sheet

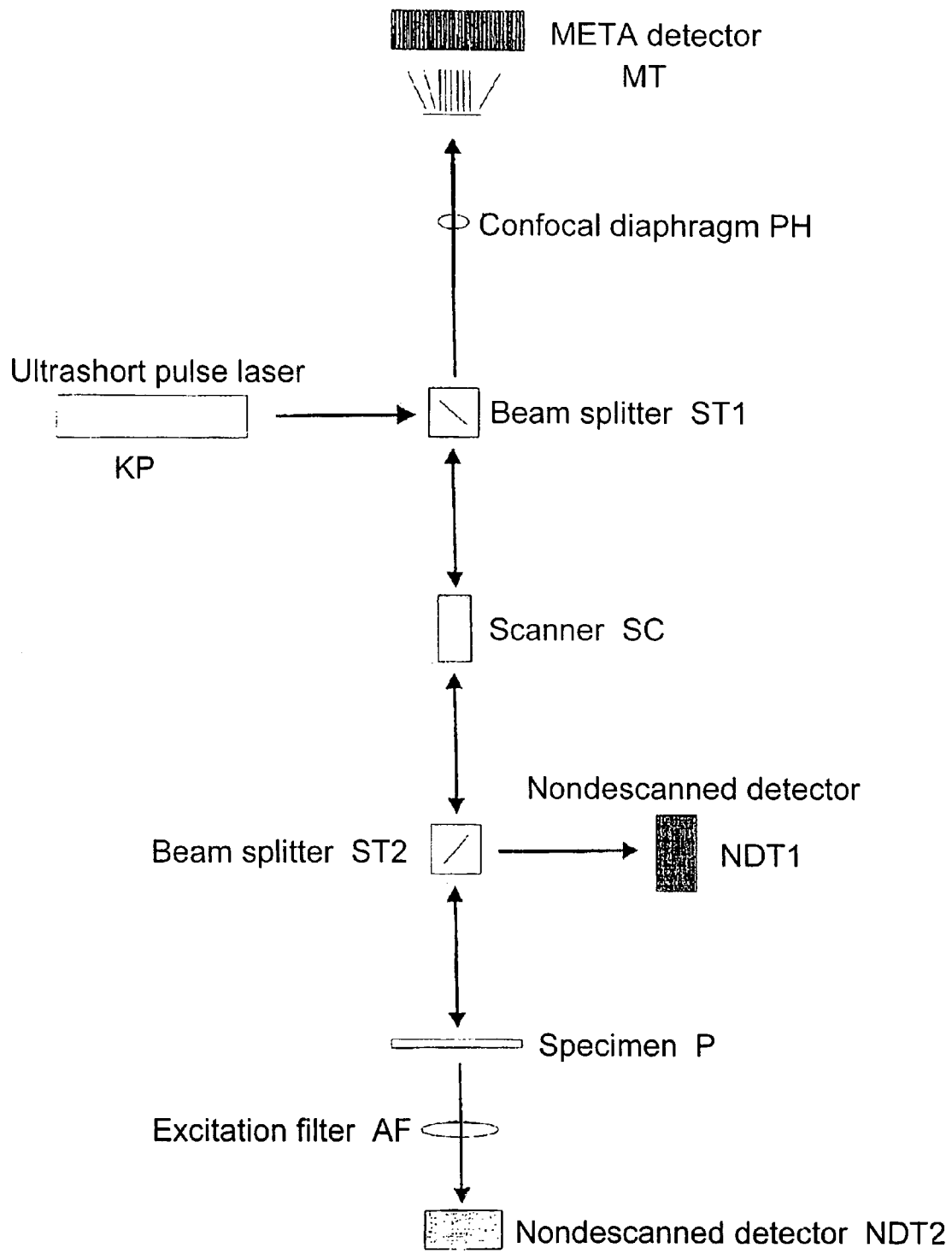

METHOD FOR THE DETECTION OF FLUORESCENT LIGHT

CROSS-REFERENCE TO RELATED APPLICATION

This application claims priority of German application No. 103 03 404.8, filed Jan. 27, 2003, the complete disclosure of which is hereby incorporated by reference.

BACKGROUND OF THE INVENTION a) Field of the Invention

The detection of individual fluorochromes in multiply labeled, highly light-scattering specimens was carried out heretofore through the selection of the excitation wavelengths in the visible region and through the use of corresponding emission filters.

b) Description of the Related Art

With overlapping emission spectra, the detection of emission spectra can be carried out with subsequent regression analysis (Schäfer patent). The detectors used for this purpose are generally PMTs which are located in the light path behind the scanning optics of the microscope. The penetration depth of the visible laser is sometimes severely limited depending on the specimen.

The use of a multiphoton laser for generation of fluorescence in dyed, highly light-scattering specimens also allows detection of the emission signals with filters. In so doing, fluorescent signals whose emission spectra overlap only slightly or not at all can be separated from one another. A sequential excitation of the individual fluorochromes with the required wavelength in connection with the detection of the respective signal (multitracking) is usually impossible in multiphoton microscopy since, in this method, a plurality of fluorochromes are often excited simultaneously with one wavelength because they have broader excitation spectra than in single photon excitation. With extensively overlapping emission spectra of the individual fluorochromes, the emission signals can also be detected spectroscopically in multiphoton microscopy by a PMT array with a dispersive element arranged upstream (U.S. Pat. No. 6,403,332) and can then be separated by regression analysis.

The problem in all of these methods is that fluorescent signals generated in deep areas of highly scattering specimens can only be detected to an insufficient extent.

OBJECT AND SUMMARY OF THE INVENTION

The primary object of the invention is to solve the stated problem by the method of the invention.

In accordance with the invention, a method for the detection and evaluation of the light generated in a fluorescing specimen by a short pulse laser comprising the steps of separately irradiating at least a first and a second fluorophore and/or a self-fluorescing specimen with different wavelengths, recording specimen light in a wavelength-dependent manner with at least one nondescanned detector as reference spectrum and carrying out a separation into individual spectra during the irradiation of at least two fluorophores and/or self-fluorescing specimens simultaneously from the measured spectrum and the reference spectra through regression analysis.

The invention thus combines the production of an excitation spectrum by means of a tunable ultrashort pulse laser with the use of nondescanned detectors (optimal scatter light detection, signal is not conducted via the scanning optics) for recording the intensities of the fluorochrome or fluorochromes at different wavelengths. These images are used to produce excitation spectra and to determine the proportions of the intensities of individual fluorochromes in a multiply labeled, highly scattering specimen by regression analysis. The combination of the use of an ultrashort pulse laser and of the nondescanned detectors makes it possible to detect excitation spectra also in highly scattering specimens and to separate the signals from extensively overlapping emission spectra.

The following steps are taken in the method:

Detection of the excitation spectra. A fluorescing specimen is illuminated by the multiphoton laser. The light beam is guided over the specimen by means of a scanner. The generated fluorescent signal is guided to a nondescanned detector via optical elements. The total intensity of the fluorescent signal is detected. The wavelength of the ultrashort pulse laser is varied in defined steps. The total intensity is detected again by the detector at every wavelength. The images of the fluorescent signal generated at each individual wavelength are stored in the sequence of detection. The excitation spectrum is determined for every fluorochrome. The fluorescence intensity of a multiply labeled specimen is determined under the same conditions (adjustment of laser intensity, scanning steps, detector adjustment). The excitation spectra of the individual fluorochromes are used to determine the proportion of fluorochromes in the multiply labeled specimen by means of regression analysis.

BRIEF DESCRIPTION OF THE DRAWING

The sole drawing is a schematic flow diagram illustrating the invention.

DESCRIPTION OF THE PREFERRED EMBODIMENTS

A tunable short pulse laser KP which irradiates a specimen P via a dichroic beam splitter ST1 and an X/Y scanning device SC is shown schematically in FIG. 1. Nondescanned detectors NDT1 and NDT2 are provided in addition to a wavelength-selective detector MT behind a confocal diaphragm PH; NDT1 is provided for excited light, including scatter light, coming from the specimen P via beam splitter ST2 and NDT2 is provided for light, including scatter light, that is generated in the specimen and goes through the specimen. In this case, an excitation filter AF is provided for blocking the excitation light. The tuning of the short pulse laser is carried out, for example, in a wavelength region of about 700–900 nm, e.g., fluorophores with an excitation maximum at about 750 nm and 800 nm are initially detected in a wavelength-dependent manner with reference to the intensity measured by NDT1 or NDT2.

When these two fluorophores are both present in a specimen, a mixed spectrum is recorded when the laser is tuned and can subsequently be separated by regression analysis.

While the foregoing description and drawings represent the present invention, it will be obvious to those skilled in the art that various changes may be made therein without departing from the true spirit and scope of the present invention.

What is claimed is:

1. A method for the detection and evaluation of the light generated in a fluorescing specimen by a short pulse laser, comprising the steps of:

separately irradiating at least a first and a second fluorophore and/or a self-fluorescing specimen with different wavelengths;
recording specimen light in a wavelength-dependent manner with at least one nondescanned detector as reference spectrum; and
carrying out a separation into individual spectra during the irradiation of at least two fluorophores and/or self-fluorescing specimens simultaneously from the measured spectrum and the reference spectra through regression analysis.

2. The method according to claim 1, wherein the wavelength of the short pulse laser is changed continuously in at least one wavelength region.

3. The method according to claim 1, wherein at least a part of the specimen is scanned and a fluorescence image of the specimen or of a portion of the specimen is detected and stored for the respective adjusted wavelength.

* * * * *